United States Patent [19]

Bayer et al.

[11] Patent Number: 4,820,532
[45] Date of Patent: Apr. 11, 1989

[54] PREPARATION OF A LOW-DUST FREE-FLOWING CHOLINE CHLORIDE POWDER

[75] Inventors: Robert Bayer, Steinsfurt; Guenter Boettger, Bad Duerkheim; Rainer Hiller, Muenster; Michael Huber, Schifferstadt; Wolfgang Koernig, Leimen; Wolfgang Fritz, Karlsruhe, all of Fed. Rep. of Germany

[73] Assignee: BASF Aktiengesellschaft, Ludwigshafen, Fed. Rep. of Germany

[21] Appl. No.: 68,061

[22] Filed: Jun. 30, 1987

[30] Foreign Application Priority Data

Jul. 16, 1986 [DE] Fed. Rep. of Germany ....... 3623922

[51] Int. Cl.$^4$ ............................................... A23K 1/00
[52] U.S. Cl. .................................... 426/74; 426/311; 426/471; 426/601
[58] Field of Search .................. 426/311, 471, 72, 74, 426/648

[56] References Cited

U.S. PATENT DOCUMENTS

| | | | |
|---|---|---|---|
| 2,765,231 | 10/1956 | Plitt | 426/311 |
| 2,879,161 | 3/1959 | Valentine et al. | |
| 2,970,911 | 2/1961 | Lorz | 426/72 |
| 3,356,569 | 12/1967 | Nicodemus et al. | 426/72 |

FOREIGN PATENT DOCUMENTS 0698606  7/1978  U.S.S.R.

Primary Examiner—R. B. Penland
Attorney, Agent, or Firm—Keil & Weinkauf

[57] ABSTRACT

A low-dust, free-flowing choline chloride powder based on natural carriers or silica, the choline chloride content on natural carriers being from 30 to 60% by weight and that on silica being from 30 to 80% by weight, based on the choline chloride powder, is prepared by a process in which (a) choline chloride solution is mixed with the carrier in the desired ratio within the stated range,
(b) the resulting mixture is sprayed continuously into a fluidized bed already containing dry choline chloride powder and is dried there at from 90° to 180° C., and
(c) the dried end product is removed from the fluidized bed and cooled to below 50° C.

7 Claims, No Drawings

PREPARATION OF A LOW-DUST FREE-FLOWING CHOLINE CHLORIDE POWDER

The present invention relates to the preparation of low-dust free-flowing choline chloride powder based on natural carrier-s or silica and having a controlled particle size distribution.

Choline is a member of the group consisting of the vitamins of the B complex and is widely used for enriching animal feeds. Because it cannot be handled and used in the free form, salts of choline are generally prepared, in particular choline chloride. Choline is indispensable in the metabolism of fats. In many animal species, choline deficiency initially leads to fatty degeneration of the liver and renal damage and subsequently to cirrhosis of the liver. In poultry, for example, deformities of joints and bones, retarded growth and increased mortality are observed.

As a pure solid, choline chloride is extremely hygroscopic. In contact with the atmosphere, the product immediately attracts water vapor and becomes liquid. For this reason, it cannot be sold as the pure substance. As a feed additive, choline chloride is used either in dissolved form (75-78% strength aqueous solution) or as a 50% strength dry powder with an inorganic or organic carrier (adsorbate). A known inorganic carrier for choline chloride is highly porous silica, which, when mixed with choline chloride and dried, gives a dry, free-flowing powder which is sold in this form. Highly absorptive, milled natural products, such as corncob flour, rice husks, malt culms and puffed starch made from wheat, corn, etc., are used as organic carriers.

Choline chloride on carriers is primarily used by small-scale consumers, who mix the animal feed before use, as required. As a rule, this procedure is carried out without excluding atmospheric moisture, ie. bags which are not emptied generally remain open until they are used again.

Since the choline chloride is added to the mixed feed in a ratio of only about 1:1,000, the particle size has to conform to narrow limits. In the case of excessively large particles, it is no longer probable that all animals, particularly chicks, will consume the same amount of active ingredient; excessively small particles makes storage and handling more difficult. Finally, there is the danger of separation in the animal feed. For these reasons, the particle size must be within certain limits.

U.S. Pat. No. 2,879,161 discloses that silica is a very suitable carrier for choline chloride since it has an extremely high adsorption capacity and can therefore absorb up to 65% by weight of choline chloride solution during mixing. After the mixing process, a white, pulverulent, free-flowing end product containing about 50% by weight of choline chloride, 33% by weight of silica and 17% by weight of water is obtained.

However, this process has the disadvantage that the concentration of only 50% by weight of choline chloride in the end product is relatively low.

A process for the preparation of choline chloride powder in which starch-containing corn is used as the carrier for choline chloride has also been disclosed. The milled corn is pretreated in an extruder under pressure and at elevated temperatures so that it is converted to puffed, porous extrudates. The extrudates are mixed with 70% strength aqueous choline chloride solution, dried to a moisture content of 12-14% and milled. The ready-prepared concentrate contains not more than 50% by weight of choline chloride (USSR Pat. No. 698,606).

However, this process has the following disadvantages:
(a) The natural carrier has to be prepared by a complicated and expensive method.
(b) Preferably, corn alone is exclusively used as the carrier.
(c) The residual moisture content of 12-14% after drying is high; by contrast, the concentration of only 50% by weight of choline chloride is low.
(d) The particle size spectrum of the end product is very fine; as a result, there is a danger of separation, and excessively rapid moisture absorption causes the storage and flow behavior to deteriorate.

It is an object of the present invention to provide choline chloride powders on silica or natural carriers which do not have the stated disadvantages.

We have found that this object is achieved, according to the invention, by a process for the preparation of a low-dust free-flowing choline chloride powder based on natural carriers or silica, the choline chloride content on natural carriers being from 30 to 60% by weight and that on silica being from 30 to 80% by weight, based on the choline chloride powder, wherein
(a) choline chloride solution is mixed with the carrier in the desired ratio within the stated range,
(b) the resulting mixture is sprayed continuously into a fluidized bed already containing dry choline chloride powder and is dried there at from 90° to 180° C., and
(c) the dried end product is removed from the fluidized bed and cooled to below 50° C.

The novel process permits the use of a silica having a mean particle size of about 80 $\mu$m and a specific surface area of 190 $m^2/g$. The end product obtained after mixing, drying and cooling has a low dust content, is free-flowing and non-hygroscopic and preferably has a particle size range of from 100 to 1,000 $\mu$m.

It is desirable to obtain a homogeneous mixture of the carrier and the choline chloride solution (78% of choline chloride and 22% of water) in the mixing process so that choline chloride is substantially present inside the carrier in the dried end product and cohesion of the end product due to the highly hygroscopic character of choline chloride is thus prevented. Where the inorganic carrier silica is used, a homogeneous mixture is obtained, for example, by preparing a suspension of 78% strength choline chloride solution and the silica at a mixing temperature of 20°-100° C. in a mixer. The suspension has, for example, a density of 1,200 $kg/m^3$ and a water content of about 22%, based on dry substance. Because the suspension is heated, the mixing time as such is less than 20 minutes. For reasons relating to process engineering, the choline chloride/silica mixture is rendered hydrophobic. The hydrophobic Ca stearate is mixed into the suspension together with the silica in an amount of 0.5% (based on dry product).

The novel process makes it possible for the moist mixture (suspension of choline chloride, silica and water) to be sprayed continuously into a fluidized bed via a two-material nozzle by means of a compressed gas and to be dried there.

In the invention, the velocity of the granules in the fluidized bed can be controlled by adding water, and the final particle size (100 < d < 1,000 $\mu$m) can be obtained by continuous particle size control (screening, and comminution of oversize; undersize and comminuted oversize are recycled to the fluidized bed).

Particularly suitable silicas are hydrophilic silicas having a particle size of from 40 to 300 μm and a specific surface area of from 100 to 300 m²/g.

Using the novel process, it is also possible to use available cheap organic carriers in which 80% of the particles have a size of from 100 to 800 μm. The concentrate obtained after impregnation, drying and cooling has a low dust content, is free-lowing and has a long shelf life and a homogeneous distribution of active ingredient. This means that the choline chloride content at the surface is lower than in prior art products and that the products are therefore substantially less hygroscopic.

Examples of natural carriers are wheat bran, corncob flour, corncobs, beet chips and rice husks. For example, where wheat bran is used, a particle size range of from 200 to 1,000 μm and a water content of less than 15% have proven useful.

Specifically, the preparation of a free-flowing, homogeneous mixture having an optimum distribution of active ingredient in the natural carrier is effected, for example, by impregnating the natural carrier with the choline chloride solution, which is, for example, 78% strength, in a mixer at from 60° to 100° C. during a very short mixing time of, for example, 20 minutes. The mixing time and the absorption of choline chloride by the natural carrier are controlled by the mixing temperature. The mixture has a moisture content of 15–19% by weight and is loose and free-flowing, and the active ingredient is completely and homogeneously taken up by the organic carrier.

For continuous feeding of the moist mixture into a fluidized bed drying apparatus, it is advantageous to use a slowly rotating double-blade screw of progressive pitch whose speed can be controlled.

For more poorly flowing or pourable moist mixtures containing a natural carrier, pneumatic or mechanical dispersing units may be preferable.

EXAMPLE 1

100 kg of choline chloride solution (78% by weight of choline chloride and 22% by weight of water) are initially taken in a mixer, and 0.5 kg of Ca stearate and 19 kg of finely divided silica (Sipernat ® 22 from Degussa) are metered into the stirred solution. After a mixing time of less than 20 minutes at a mixing temperature of from 60° to 100° C., the suspension is dispersed continuously into a fluidized bed via a two-material nozzle by means of compressed gas, and is dried there. The dried end product is then cooled to less than 50° C. in a product cooler to give a low-dust, free-flowing choline chloride powder which does not stick together in the air and contains 80% by weight, based on dry material, of choline chloride on silica.

EXAMPLE 2

100 kg of wheat bran are initially taken in a mixer at a low rotary speed, and 169.5 kg of choline chloride solution (78% by weight of choline chloride and 22% by weight of water) are metered in. After an impregnation time of less than 20 minutes at a mixing temperature of 60°–100° C., the loose, free-flowing moist organic material is discharged into an intermediate hopper and is continuously dispersed from there by means of a double-blade screw into a fluidized bed drying apparatus. The concentrate dried in the fluidized bed is cooled in a product cooler to below 50° C. and then screened, and the oversize obtained is comminuted in a mill in a gentle manner which produces little dust.

The process gives a low-dust free-flowing product having a homogeneous distribution of active ingredient and a particle size spectrum in which 90% of the particles are in the range from 200 to 1,000 μm.

The content of active ingredient is 60% by weight, based on the dry weight of the organic carrier.

We claim:

1. A process for the preparation of a low-dust, free-flowing powder containing choline chloride and a natural organic carrier or a silica carrier which consists essentially of the steps:
    (a) mixing an aqueous choline chloride solution with a natural carrier or a porous silica carrier in the ratio of 70 to 40% by weight of choline chloride and 30 to 60% by weight of a natural carrier, or 70 to 20% by weight to choline chloride and 30 to 80% by weight of silica to form a moist mixture;
    (b) spraying the mixture from step (a) continuously into a fluidized bed, said bed already containing added dry choline chloride powder, and drying the mixture within the bed at a temperature of from 90° to 180° C.; to form a powder containing choline chloride and a natural organic carrier or a silica carrier and
    (c) continuously removing the powder from the fluidized bed and cooling the powder to below 50° C.;
    (d) controlling the particle size of the components of the mixture to produce a low dust, free flowing powder having a final particle size range of 100–1000 μm.

2. The process of claim 1, wherein finely divided silica is used as the carrier having a mean particle size of from 40 to 300 μm and a specific surface area of from from 100 to 300 m²/g.

3. The process of claim 2, wherein the particle size of the choline chloride powder plus silica is brought to 100–1,000 μm by screening the particles, milling the oversized particles and recycling the undersized particles to the fluidized bed.

4. The process of claim 1, wherein the moist mixture obtained in stage (a) and containing choline chloride and silica is sprayed continuously into the fluidized bed via a two-material nozzle by means of compressed gas.

5. The process of claim 1, wherein comminuted beet chips, wheat bran, corncob flour, corncobs or rice husks in which 80% by weight of the particles have a size of from 150 to 800 μm is or are used as the carrier.

6. The process of claim 1, wherein the moist mixture containing a natural carrier and obtained as described in stage (a) ismetered continuously into the fluidized bed via a slowly rotating twin-blade screw.

7. The process of claim 1, wherein the particle size of 90% by weight of the choline chloride powder containing a natural carrier is brought to 200–1,000 μm by a prodecure in which, after screening the oversized particles are comminuted by milling and the undersized particles are recycled to the fluidized bed.

* * * * *